(12) United States Patent
Gartenhaus

(10) Patent No.: US 7,811,561 B1
(45) Date of Patent: Oct. 12, 2010

(54) MCT-1, A HUMAN ONCOGENE

(76) Inventor: Ronald B. Gartenhaus, 52 Southwood Dr., Cherry Hill, NJ (US) 08003

( * ) Notice: Subject to any disclaimer, the term of this patent is extended or adjusted under 35 U.S.C. 154(b) by 699 days.

(21) Appl. No.: 09/709,131

(22) Filed: Nov. 10, 2000

Related U.S. Application Data

(63) Continuation of application No. PCT/US99/10184, filed on May 10, 1999.

(60) Provisional application No. 60/085,029, filed on May 11, 1998.

(51) Int. Cl.
*A61K 39/395* (2006.01)

(52) U.S. Cl. .................................................. 424/130.1

(58) Field of Classification Search .............. 530/387.1, 530/350
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 4,663,308 A | 5/1987 | Saffran et al. | |
| 4,777,049 A | 10/1988 | Magruder et al. | |
| 4,889,806 A | 12/1989 | Olson et al. | |
| 5,767,248 A | 6/1998 | Roses et al. | |
| 5,876,930 A | 3/1999 | Livak et al. | |
| 5,935,781 A | 8/1999 | Poirier | |
| 6,013,431 A | 1/2000 | Söderlund et al. | |
| 6,153,740 A * | 11/2000 | Young et al. ................ | 536/23.5 |
| 6,479,483 B2 * | 11/2002 | Bos et al. ................... | 514/227.8 |
| 6,783,961 B1 * | 8/2004 | Edwards et al. ............ | 435/91.1 |
| 2003/0105000 A1 * | 6/2003 | Pero et al. ................... | 514/12 |

FOREIGN PATENT DOCUMENTS

WO    WO 01/77124 A2    10/2001

OTHER PUBLICATIONS

Bowie et al (Science, 1990, 257:1306-1310).*
Lazar et al (Molecular and Cellular Biology, 1988, 8:1247-1252).*
Burgess et al ( J of Cell Bio. 111:2129-2138, 1990).*
Scott et al (Nature Genetics, 1999, 21:440-443).*
Bork (Genome Research, 2000,10:398-400).*
Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-1802).*
Embleton et al (Immunol Ser, 1984, 23:181-207).*
Hsu (in Tissue Culture Methods and Applications, Kruse and Patterson, Eds, 1973, Academic Press, NY, see abstract, p. 764-767).*
Pollack et al (Nature Genetics, 1999, 23:41-46).*
Gura (Science, 1997, 278:1041-1042).*
Jain (Sci. Am., 1994, 271:58-65).*
Curti (Crit. Rev. in Oncology/Hematology, 1993, 14:29-39).*
Baker et al., J. Appl. Physiol., 1998, 84: 987-997.*
Cakarovski et al., Int. J. Cancer, 2004, 110:610-616.*
Prosniak et al., Cancer Res., Oct. 1998, 58:4233-4237.*
Delghandi et al., 1999, Acta Cardiol. 54(4):215-225.
Gajra et al., 1997, Human Biolology 69(5):629-640.
L. Kostrikis et al., 1998, Science Magazine, 279(5354)1-9.
Andersen et al., 1997, EMBO J., 16:958,967.
Baldin et al., 1993, Genes Develop., 7:812-821.
Buckley et al., 1993, Oncogene, 8:2127-2133.
Harper et al., 1995, Mol. Biol. Cell, 6:387-400.
Hiyama et al., 1997, Oncogene, 14:2533-2542.
Hoglund et al., 1996, Blood, 87:324-330.
Jiang et al., 1993, Oncogene, 8:3447-3457.
Keyomarsi et al., 1993, Proc. Natl. Acad. Sci. USA, 90:1112-1116.
Leach et al., 1993, Cancer Res., 53:1986-1989.
Lovec et al., 1994, Oncogene, 9:323-326.
Nigg, 1996, Curr. Opin. Cell Biol., 8:312-317.
Sherr, 1994, Cell, 79:551-555.
Sherr, 1993, Cell, 73:1059-1065.
Wang et al., 1994, Nature, 369:669-671.
Xiong et al., 1993, Nature, 366:701-704.
Zhang et al., 1993, Mol. Biol. Cell, 4:897-906.
Zhang et al., 1994, Genes Develop., 8:1750-1758.

\* cited by examiner

*Primary Examiner*—Larry R Helms
*Assistant Examiner*—Hong Sang
(74) *Attorney, Agent, or Firm*—Hodgson Russ LLP

(57) ABSTRACT

A novel gene, designated MCT-1 (for Multiple Copies in T-cell malignancy), is provided. A protein encoded by MCT-1, designated MCT-1, is also provided. Antisense oligonucleotides complementary to or homologous with a portion of MCT-1, substantially purified MCT-1, and methods of determining whether a cell is a tumor cell are also provided. The invention also includes monoclonal and polyclonal antibody preparations which bind with specificity to MCT-1. The invention further includes methods of determining whether a compound or a gene product is a modulator of MCT-1 expression, a method of reducing MCT-1 expression in a cell, and a method of conferring a growth advantage on a cell.

1 Claim, 4 Drawing Sheets

Fig. 1A

```
  1 GCTACCTCCA ACTGCTGAGG AACCGGTTGC CTAAAAGGAG CCGGCAAAAG
 51 CGCCTACGTG GAGTCCAGAG GAGCGGAAGT AGTCAGATTT GACTGAGAGC
101 CGTAAAGCGC GGCTGGCTCT CGTTTCCGG ATAACGACTA CAGCTCCGAC
151 TGTCAGTGCC GGCCTTCCTC GTGTGAGGGG ATCTGCCGGA CCCCTGCAAA
201 TTCAATTTCT TTCCCATTCC GGGCCCTTCC CTATCGTCGC CCCCTTCACC
251 TTGGATCATG TTCAAGAAAT TTGATGAAAA AGAAAATGTG TCCAACTGCA
301 TCCAGTTGAA AACTTCAGTT ATTAAGGGTA TTAAGAATCA ATTGATAGAG
351 CAATTTCCAG GTATTGAACC ATGGCTTAAT CAAATCATGC CTAAGAAAGA
401 TCCTGTCAAA ATAGTCCGAT GCCATGAACA TATAGAAATC CTTACAGTAA
451 ATGGAGAATT ACTCTTTTTT AGACAAAGAG AAGGGCCTTT TTATCCAACC
501 CTAAGATTAC TTCACAAATA TCCTTTTATC CTGCCACACC AGCAGGTTGA
551 TAAAGGAGCC ATCAAATTTG TACTCAGTGG AGCAAATATC ATGTGTCCCA
601 GGCTTAACTT CTCCTGGAGC CCTGCTATGT TAGATACCAT TTATCCAACC
651 TGTTGCTATC ATGGCAGAAG GAAAACAGCA TGCTCTATGT GTTGGAGTCA
701 TGAAGATGTC TGCAGAAGAC ATTGAGAAAG TCAACAAAGG AATTGGCATT
751 GAAAATATCC ATTATTTAAA TGATGGGCTG TGGCATATGA AGACATATAA
801 ATGAGCCTCA GAAGGAATGC ACTTGGGCTA AATATGGATA TTGTGCTGTA
851 TCTGTGTTTG TGTCTGTGTG TGACAGCATG AAGATAAATGC CTGTGGTTAT
901 GCTGAATAAA TTCACCAGAT GCTAAAAAAA AAAAAAAAAA AAAA
```

Glycosylation Site          Tyr Phosphorylation Site

```
  1 MFKKFDEKEN VSNCIQLKTS VIKGIKNQLI EQFPGIEPWL NQIMPKKDPV
 51 KIVRCHEHIE ILTVNGELLF FRQREGPFYP TLRLLHKYPF ILPHQQVDKG
101 AIKANIMCPG LTSPGAKLYP AAVDTIVAIM AEGKQHALCV GVMKMSAEDI
151 EKVNKGIGIE NIHYLNDGLW HMKTYK
```

PKC Phosphorylation Sites      CK2 Phosphorylation Site

Fig. 3

```
MCT-1     8KENVSNCIQLKTSVIKGIKNQLIEQFPGIEPWLNQIMPKKDPVK 51
           |||  |::  |   :: ||:|::|  —|:|::  |:|:|:|||:
Cyclin H 239KEN.RTCLSQLLDIMKSMRN.LVKKYE..PPRSEEVAVLKQ..K277

MCT-1    52IVRCHEHIEILTVN 65
           : |||  |:  |::|
Cyclin H 278LERCHS.AE.LALN288
```

```
  1 GCTACCTCCA ACTGCTGAGG AACCGGTTGC CTAAAAGGAG CCGGCAAAAG
 51 CGCCTACGTG GAGTCCAGAG GAGCGGAAGT AGTCAGATTT GACTGAGAGC
101 CGTAAAGCGC GGCTGGCTCT CGTTTTCCGG ATAACGACTA CAGCTCCGAC
151 TGTCAGTGCC GGCCTTCCTC GTGTGAGGGG ATCTGCCGGA CCCCTGCAAA
201 TTCAATTTCT TTCCCATTCC GGGCCCCTCC CTATCGTCGC CCCCTTCACC
251 TTGGATCATG TTCAAGAAAT TTGATGAAAA AGAAAATGTG TCCAACTGCA
301 TCCAGTTGAA AACTTCAGTT ATTAAGGGTA TTAAGAATCA ATTGATAGAG
351 CAATTTCCAG GTATTGAACC ATGGCTTAAT CAAATCATGC CTAAGAAAGA
401 TCCTGTCAAA ATAGTCCGAT GCCATGAACA TATAGAAATC CTTACAGTAA
451 ATGGAGAATT ACTCTTTTTT AGACAAAGAG AAGGGCCTTT TTATCCAACC
501 CTAAGATTAC TTCACAAATA TCCTTTTATC CTGCCACACC AGCAGTTGA
551 TAAAGGAGCC ATCAAATTTG TACTCAGTGG AGCAAATATC ATGTGTCCAG
601 GCTTAACTTC TCCTGGAGCT AAGCTTTACC CTGCTGCAGT AGATACCATT
651 GTTGCTATCA TGGCAGAAGG AAAACAGCAT GCTCTATGTG TTGGAGTCAT
701 GAAGATGTCT GCAGAAGACA TTGAGAAAGT CAACAAAGGA ATTGGCATTG
751 AAAATATCCA TTATTTAAAT GATGGGCTGT GGCATATGAA GACATATAAA
801 TGAGCCCTAG AAGGAATGCA CTTGGGCTAA ATATGGATAT TGTGCTGTAT
851 CTGTGTTTGT GTCTGTGTGT GACAGCATGA AGATAATGCC TGTGGTTATG
901 CTGAATAAAT TCACCAGATG CTAAAAAAAA AAAAAAAAAA AAA
```

MCT-1, A HUMAN ONCOGENE

CROSS REFERENCE TO RELATED APPLICATIONS

This application is a continuation of international patent application number PCT/US99/10184 (International Publication Number WO 99/58640), which was filed on May 10, 1999. This application is entitled to the benefit of U.S. provisional patent application 60/085,029, which was filed on May 11, 1998, now abandoned.

FIELD OF THE INVENTION

The field of the invention is oncogenes and tumorigenesis.

BACKGROUND OF THE INVENTION

Tumorigenesis is a multi-step process wherein a causal relationship exists between accumulation of genetic abnormalities and aggressive clinical behavior of tumor cells (Fearon et al., 1990, Cell 61:759-767; Callfano et al., 1996, Cancer Res 56:2488-2492). In many tumors, amplification of critical growth-inducing genes is observed, coupled with deregulated expression of G1 cyclins and their cognate cdk partners (Lammie et al, 1991, Oncogene 6:439-444; Motokura et al., 1991, Nature 350:512-515).

Distinct complexes are formed between cyclins and one or more cognate cyclin dependent kinases (cdk's) at different phases of the cell cycle, and activation of the cognate kinases occurs following complex formation. Progression of cells through the late G1 phase of the cell cycle is controlled by G1 cyclins, including D and E type cyclins and their cognate cdk's (Sherr, 1994, Cell 79:551-555). Phosphorylation of the retinoblastoma gene product (Rb) and related gene products facilitates entry into S phase. The D type cyclins are known to form complexes with either cdk4 or cdk6 (Baldin et al., 1993, Genes Develop. 7:812-821).

Expression of G1 cyclins and their cognate cdk partners is often deregulated in human tumor cells. Overexpression of cyclin D1 can shorten the G1 interval of the cell cycle, and thereby reduce cell size and/or transform cells, both in vitro and in vivo (Jiang et al., 1993, Oncogene 8:3447-3457; Lovec et al., 1994, Oncogene 9:323-326).

Primary cutaneous lymphomas are among the more common presentations of extra-nodal non-Hodgkins lymphomas (NHLs). NHLs include adult T-cell leukemia/lymphoma (ATLL) and cutaneous T-cell lymphoma (CTCL). The etiologic agent of ATLL, HTLV-1, has been known for years. In contrast, the molecular pathogenesis of CTCL, the most frequent type of cutaneous lymphoma, is not well characterized at present. A recent report demonstrated rearrangement of the tal-1 and lyt-10 genes in a small subset of CTCL cells, but no consistent molecular lesions were detected (Neri et al., 1995, Blood 86:3160-3172).

Development of effective anti-cancer or anti-tumorigenic treatments would be facilitated by identification of one or more genes, mal-expression of which is associated with the onset or progression of tumorigenesis. The present invention provides the identity and the coding sequence of such a gene.

BRIEF SUMMARY OF THE INVENTION

The invention relates to an isolated nucleic acid which binds with high specificity with a portion of the mRNA-coding region of a human MCT-1 gene. In one embodiment, the mRNA-coding region of the gene has the nucleotide sequence SEQ ID NO: 7. For example, the portion may have a nucleotide sequence selected from the group consisting of at least about 20 or 25 consecutive nucleotide residues of SEQ ID NO: 7 and at least about 20 or 25 consecutive nucleotide residues of the sequence complementary to SEQ ID NO: 7. In another embodiment, the isolated nucleic acid has a sequence which is either at least about 75% homologous with the portion or at least about 75% complementary to the portion. For example, the isolated nucleic acid may have a sequence which is either at least about 95% or 100% homologous with the portion or at least about 95% or 100% complementary to the portion.

The isolated nucleic acid of the invention may comprises one or more modified internucleoside linkages.

The invention includes a vector comprising the isolated nucleic acid of the invention. In the vector, the isolated nucleic acid may be operably linked with a promoter. For example, a portion comprising nucleotide residues 258-800 of SEQ ID NO: 7 may be operably linked with a promoter.

The invention also includes a pair of isolated nucleic acids of the invention wherein one of the pair is complementary to a first portion of the mRNA-encoding region and the other of the pair is homologous with a second portion of the mRNA-encoding region.

The invention further includes an isolated molecular beacon nucleic acid comprising a first portion and a second portion. The first portion binds with high specificity with a region of the mRNA-coding region of a human MCT-1 gene. The second portion anneals with the first portion to a lesser degree when the first portion is not annealed with the region than when the first portion is annealed with the region. The first portion has one of a fluorophore-quencher pair associated therewith, and the second portion has the other of the fluorophore-quencher pair associated therewith. The molecular beacon nucleic acid of the invention fluoresces in the presence of the region to a greater degree than in the absence of the region.

In another aspect, the invention relates to an isolated polypeptide having an amino acid sequence which comprises at least about ten or fifteen consecutive amino acid residues of SEQ ID NO: 8. The amino acid sequence of the isolated polypeptide may, of course, be the entirety of SEQ ID NO: 8. In one embodiment, the polypeptide is substantially purified.

The invention also relates to a method of reducing MCT-1 expression in a cell. This method comprises providing an isolated nucleic acid which binds with high specificity with a portion of the mRNA-coding region of a human MCT-1 gene to the cell. Expression of MCT-1 in the cell is thereby reduced.

The invention further relates to a method of increasing MCT-1 production in a cell. This method comprises providing an isolated nucleic acid to the cell. The isolated nucleic acid comprises a promoter operably linked with a portion of the mRNA-coding region of an MCT-1 gene. Production of MCT-1 in the cell is increased by providing the isolated nucleic acid to the cell. In one embodiment of this method, the portion comprises nucleotide residues 258-800 of SEQ ID NO: 7.

The invention still further relates to a method of determining whether a test compound is a modulator of MCT-1 expression. This method comprises culturing a first cell which overexpresses MCT-1 in the presence of the test compound and comparing MCT-1 expression in the first cell with MCT-1 expression in a second cell of the same type cultured in the absence of the test compound. A difference between MCT-1 expression in the first cell and MCT-1 expression in the second cell is an indication that the test compound is a modulator of MCT-1 expression.

The invention also includes a method of determining whether a gene product is a modulator of MCT-1 expression. This method comprises expressing an isolated nucleic acid encoding the gene product in a first cell which overexpresses MCT-1 and comparing MCT-1 expression in the first cell with MCT-1 expression in a second cell of the same type. The isolated nucleic acid is not expressed in the second cell. A difference between MCT-1 expression in the first cell and MCT-1 expression in the second cell is an indication that the gene product is a modulator of MCT-1 expression.

The invention further includes a method of determining whether a cell is a tumor cell. This method comprises comparing MCT-1 expression in the cell and MCT-1 expression in a non-tumor cell. A difference between MCT-1 expression in the cell and MCT-1 expression in the non-tumor cell is an indication that the cell is a tumor cell.

In another aspect, the invention relates to a method of determining whether a cell is a tumor cell. This method comprises comparing MCT-1 copy number in the cell and MCT-1 copy number in a non-tumor cell. A difference between MCT-1 copy number in the cell and MCT-1 copy number in the non-tumor cell is an indication that the cell is a tumor cell.

The invention also includes a method of conferring a growth advantage on a cell. This method comprises providing an isolated nucleic acid to the cell. The isolated nucleic acid comprises a promoter operably linked to a portion of the mRNA-coding region of an MCT-1 gene. By providing this isolated nucleic acid to the cell, a growth advantage is conferred on the cell.

BRIEF DESCRIPTION OF THE DRAWINGS

FIG. 1, comprising FIGS. 1A and 1B is a pair of sequences. FIG. 1A is a nucleotide sequence (SEQ ID NO: 1) of a 944 nucleotide residue human cDNA molecule described in Example 1, which was originally thought to encode MCT-1. It is now known that the cytosine residue at position 599 is not present in the sequence, as indicated in the corrected sequence listed in FIG. 5A. FIG. 1B is the deduced amino acid sequence (SEQ ID NO: 2) of the protein encoded by the nucleotide sequence listed in FIG. 1A. Single-letter codes are used to identify amino acid residues. It is now known that the amino acid sequence of residues 115+ of MCT-1 differs from that listed here, as indicated in the corrected sequence listed in FIG. 5B.

FIG. 3 is a listing of the amino acid sequence of MCT-1 (SEQ ID NO: 2), wherein putative post-translational modification sites are indicated. A putative glycosylation site, a putative Tyr phosphorylation site, two putative PKC phosphorylation sites, and a putative CK2 phosphorylation site are indicated.

FIG. 4 is a comparison of a portion (SEQ ID NO: 9) of the amino acid sequence of MCT-1 with a similar portion (SEQ ID NO: 10) of the amino acid sequence of Cyclin H. A solid bar between adjacent amino acid residues indicates identity; double dots between adjacent amino acid residues indicates conservative replacement; single dots between adjacent amino acid residues indicates amino acid residues which are structurally similar.

FIG. 5, comprising FIGS. 5A and 5B, is a pair of sequence listings. The nucleotide sequence (SEQ ID NO: 7) of the cDNA encoding MCT-1 is listed in FIG. 5A. The amino acid sequence (SEQ ID NO: 8) of MCT-1 is listed in FIG. 5B. The underlined sequence is the polyadenylation signal.

DETAILED DESCRIPTION

Figures 5A, 5B:
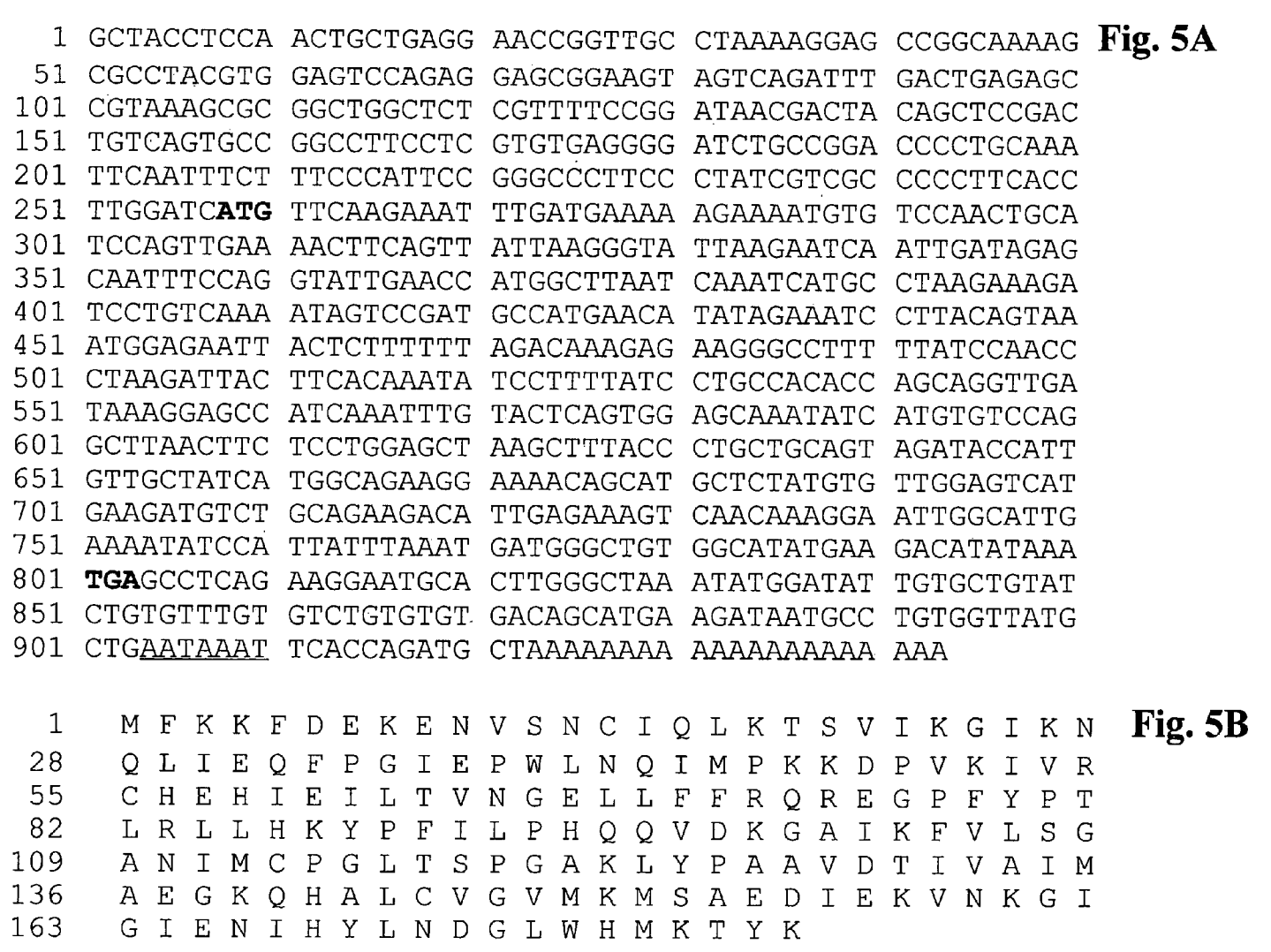
Figure 2:
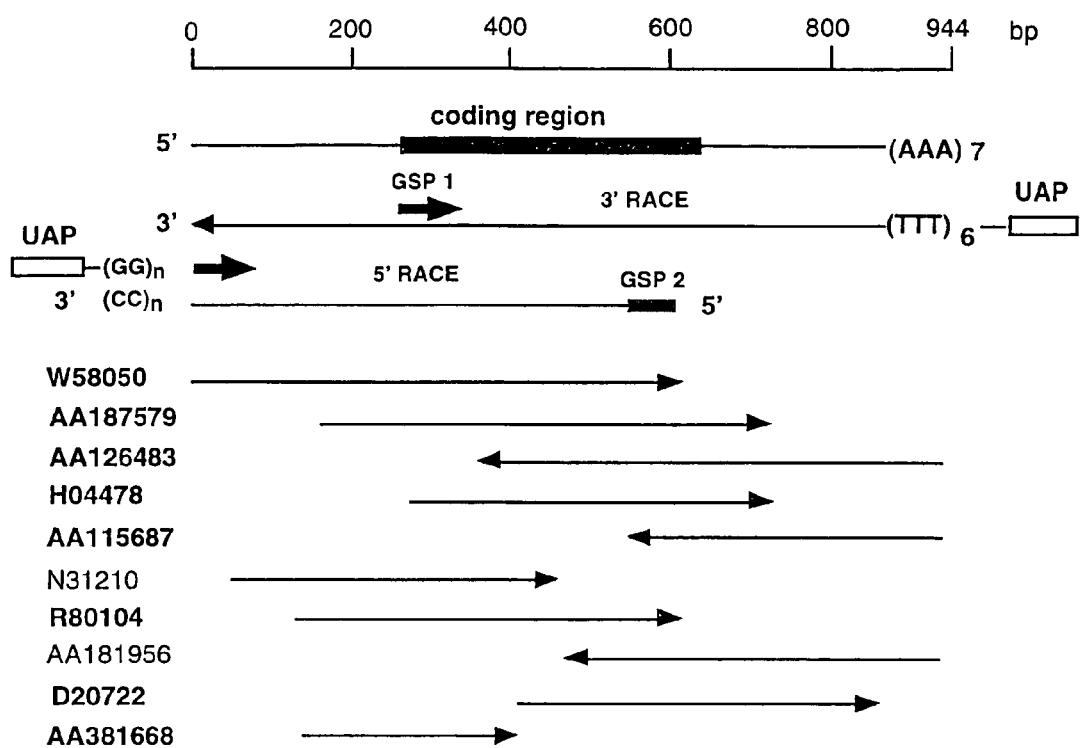
FIG. 2 is a diagram which depicts various polynucleotides. The top line is a scale which indicates polynucleotide length, measured in nucleotide residues. The second line depicts MCT-1 mRNA; the region of the molecule corresponding to the coding region of MCT-1 is indicated by a thick bar. The third line depicts a 3'-RACE (rapid amplification of cDNA ends) product prepared using MCT-1 mRNA. The fourth line depicts a 5'-RACE product prepared using MCT-1 mRNA. The fifth through fourteenth lines represent individual expressed sequence tags (ESTs) which exhibited homology with MCT-1.

The invention relates to the discovery of a gene, herein designated MCT-1 (for Multiple Copies in T-cell malignancy), which is overexpressed in certain tumor cells. For example, MCT-1 is overexpressed in T-cell tumor cells, such as cells obtained from a patient afflicted with cutaneous T-cell leukemia (CTCL; i.e. the Hut 78 cell line). Genomic analysis of such cells indicated that the MCT-1 gene is present in an increased copy number in tumor cell lines established from a patient. The MCT-1 gene comprises an open reading frame (ORF) which encodes a 181-amino acid residue polypeptide, herein designated MCT-1. A cDNA molecule comprising the ORF of MCT-1 has been isolated (SEQ ID NO: 7; listed in FIG. 5A). MCT-1 has the amino acid sequence SEQ ID NO: 8, and is listed in FIG. 5B.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The terms "nucleic acid" and "polynucleotide" are used interchangeably herein and mean any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

A nucleic acid has a "modified internucleoside linkage" if at least one phosphodiester bond in the nucleic acid is replaced by an alternative chemical linkage such as, for example, a phosphoramidate linkage.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked with the coding region of a gene is able to promote transcription of the coding region.

As used herein, the term "promoter" means a DNA sequence which is required for expression of a gene operably linked to the promoter. In some instances, the promoter may be the core promoter sequence and in other instances, the promoter may also include an enhancer sequence and other regulatory elements which are required for expression of the gene in, for example, an inducible, suppressible, or tissue-specific manner.

A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

An "mRNA-coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 50% homology. When every subunit position in the two molecules is occupied by the same monomeric subunit, the two molecules are said to be "completely" homologous.

"Complementary" refers to the broad concept of subunit sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion, in which instance the two portions are described as being "completely" complementary.

A first oligonucleotide anneals with a second oligonucleotide "with high stringency" if the two oligonucleotides anneal under high stringency hybridization conditions.

By "high stringency hybridization conditions" is meant those oligonucleotide hybridizing conditions that (1) employ low ionic strength and high temperature for washing, for example, 0.015 molar NaCl, 1.5 millimolar sodium citrate, and 0.1% (w/v) sodium dodecyl sulfate (SDS) at 50° C.; (2) employ during hybridization a denaturing agent such as formamide, for example, 50% (v/v) formamide, 0.1% (w/v) bovine serum albumin, 0.1% (w/v) Ficoll, 0.1% (w/v) polyvinylpyrrolidone, and 50 millimolar sodium phosphate buffer at pH 6.5 with 750 millimolar NaCl, 75 millimolar sodium citrate at 42° C.; or (3) employ 50% (v/v) formamide, 5×SSC (0.75 molar NaCl, 75 millimolar sodium pyrophosphate, 5×Denhardt's solution, sonicated salmon sperm DNA (50 micrograms per milliliter), 0.1% (w/v) SDS, and 10% (w/v) dextran sulfate at 42° C., with washes at 42° C. in 0.2×SSC and 0.1% (w/v) SDS. Under stringent hybridization conditions, only highly complementary nucleic acids hybridize. Preferably, such conditions prevent hybridization of nucleic acids having 1 or 2 mismatches out of 20 contiguous nucleotides.

A "portion" and a "region" of a polynucleotide are used interchangeably to mean at least at least about twenty sequential nucleotide residues of the polynucleotide. It is recognized that a portion of a polynucleotide may include every nucleotide residue of the polynucleotide.

As used herein, an "amplified genomic sequence" is a sequence of nucleotide residues in the genome of a mammal such as a human which is present in the genome in a greater number of copies than the number of copies normally present in the genome.

The term "substantially purified" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

As used herein, the term "pharmaceutically acceptable carrier" means a chemical composition with which the active ingredient(s) may be combined and which, following the combination, can be used to administer the active ingredient(s) to a subject.

As used herein, the term "physiologically acceptable" ester or salt means an ester or salt form of the active ingredient(s) which is compatible with any other ingredients of the pharmaceutical composition and which is not deleterious to the subject to which the composition is to be administered.

The Isolated Nucleic Acid of the Invention

The invention relates to an isolated nucleic acid which binds with high specificity with a portion of the mRNA-coding region of a human MCT-1 gene. This region is listed in FIG. 5A (SEQ ID NO: 7). The isolated nucleic acid may be homologous with or complementary to a portion of SEQ ID NO: 7, and includes nucleotide residues 258-800 of SEQ ID NO: 7, which encode the amino acid sequence of MCT-1 (SEQ ID NO: 8). The portion may be homologous with or complementary to the entire mRNA-coding region, or at least about twenty, twenty-five, thirty, fifty, or more nucleotide residues thereof. It is understood that the isolated nucleic acid of the invention need not be completely homologous with or completely complementary to the mRNA-coding region in order for it to bind with high specificity therewith. Instead, the isolated nucleic acid need only be mostly complementary or homologous. For example, the isolated nucleic acid may be 75%, 90%, 95%, or, preferably, completely complementary to or homologous with the mRNA-coding region.

In an important embodiment of the present invention, the isolated nucleic acid has a sequence which is homologous with nucleotide residues 258-800 of SEQ ID NO: 7. This portion of the mRNA-coding region encodes the amino acid sequence of MCT-1 protein. By operably linking this portion, or at least most residues thereof (e.g. the nucleotide residues encoding amino acid residues 8-65 of MCT-1) with a transcriptional promoter, the resulting nucleic acid may be used to generate MCT-1 protein, either by providing the nucleic acid to an organism capable of expressing it or by using an in vitro transcription/translation mixture. Because this portion does not include the terminator codon (i.e. nucleotide residues 801-803 of SEQ ID NO: 7), a termination sequence should be operably associated with the portion if the portion is to be expressed. Of course, it is understood that additional amino acid-specifying codons may be inserted between the portion and either or both of the promoter region or the termination sequence, whereby a fusion protein comprising at least a portion of the amino acid sequence of MCT-1 is generated upon expression of the nucleic acid. The fusion protein may, for example, comprise a portion of a hemagglutinin (as described herein in Example 2) or a hexa-histidine polypeptide sequence for facilitating purification of the expressed protein by metal- (e.g. nickel-) affinity chromatography.

Given the nucleotide sequence of the mRNA-coding region of MCT-1 provided herein, one skilled in the art can generate a polynucleotide capable of annealing with either the coding or the non-coding strand of MCT-1 or with RNA, such as mRNA, transcribed therefrom. Such oligonucleotides are useful for binding to mRNA and single-stranded DNA to modulate transcription and translation thereof, to facilitate specific detection thereof, or to amplify a sequence using a PCR method, for example.

For example, an antisense oligonucleotide capable of annealing with the coding strand of the mRNA-coding region of MCT-1 (and therefore also capable of annealing with an mRNA molecule generated by transcribing MCT-1) is made by generating an oligonucleotide having a nucleotide sequence complementary to a portion of SEQ ID NO: 7. An antisense oligonucleotide capable of annealing with the non-coding strand of the mRNA-coding region of MCT-1 is made by generating an oligonucleotide having a nucleotide sequence homologous with a portion of SEQ ID NO: 7. Preferably, the antisense oligonucleotide is either complementary to or homologous with at least about twenty sequential nucleotide residues of SEQ ID NO: 7, and preferably to or with about twenty-five, thirty, fifty, or more sequential nucleotide residues. As is understood in the art, regions of homology between two polynucleotides may be interrupted by one or more non-homologous base pairs. Thus, the antisense oligonucleotide may comprise one or more nucleotide residues which are not homologous or complementary to the portion of SEQ ID NO: 7. An antisense oligonucleotide complementary to a portion of SEQ ID NO: 7 is useful for inhibiting translation of an mRNA molecule generated by transcribing MCT-1. An antisense oligonucleotide homologous with a portion of SEQ ID NO: 7 is useful for inhibiting transcription of MCT-1.

In another important embodiment, the isolated nucleic acids of the invention are supplied in pairs which are useful for amplification of all or part of the sequence of the human MCT-1 gene. Design and use of such primer pairs for amplification of nucleic acids are well known in the art and are fully enabled by the listing herein of SEQ ID NOs: 1 and 7. Such primer pairs will generally comprise a first isolated nucleic acid which is complementary to a first portion of SEQ ID NO: 7 and a second isolated nucleic acid which is complementary to a second portion of SEQ ID NO: 7.

It is understood that the sole sequence difference between SEQ ID NO: 7 and SEQ ID NO: 1 is the presence of an additional cytosine residue in SEQ ID NO: 1 at position 599 (i.e. between residues 598 and 599 of SEQ ID NO: 7). Thus, SEQ ID NO: 1 may be used in place of SEQ ID NO: 7 herein, except that use of SEQ ID NO: 7 is preferred when the identity of the residue at position 599 is critical.

The isolated nucleic acid of the invention may be delivered to a cell using a vector. The vector may comprise the isolated nucleic acid operably linked with one or more of a promoter sequence, a transcriptional or translational regulatory sequence, a membrane-directing or "signal" sequence, and a terminator sequence, or it may not be operably linked with any of these. Thus, the isolated nucleic acid may be merely delivered to a cell by the vector, be delivered to the cell in a form in which it is transcribed in the cell, be delivered in a form in which it is transcribed and translated in the cell, or be delivered in a form in which it is transcribed, translated, and directed to a particular location relative to the cell (e.g. to the nucleus or to the exterior of the cell). All of these sequences and their use are well known in the art. The vector may, for example, be a viral vector or a non-viral vector such as a plasmid.

Numerous modifications of oligonucleotides are known in the art, and these modifications, as applied to the isolated nucleic acid of the invention, are also included in the invention. For example, oligonucleotides comprising altered sugar moieties, non-natural inter-sugar linkages, phosphorothioate moieties, methyl phosphonate moieties, short chain alkyl moieties, cycloalkyl moieties, and the like are known.

It is not intended that the present invention be limited by the nature of the nucleic acid employed. The isolated nucleic acid of the invention may be native or synthesized nucleic acid. The isolated nucleic acid may be obtained from a viral, bacterial, animal, plant, or synthetic source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, *J. Biol. Chem.* 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, Oligonucleotide Synthesis: A Practical Approach (IRL Press, Oxford, England)). RNAs may be produce in high yield via in vitro transcription using plasmids such as SP65 (Promega Corporation, Madison, Wis.).

In some circumstances, as where increased nuclease stability is desired, isolated nucleic acids having modified internucleoside linkages may be preferred. Isolated nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH$_2$—S—CH$_2$—), dimethylene-sulfoxide (—CH$_2$—SO—CH$_2$—), dimethylene-sulfone (—CH$_2$—SO$_2$—CH$_2$—), 2'-O-alkyl, and 2'-deoxy-2'-fluoro phosphorothioate internucleoside linkages are well known in the art (e.g. Uhlmann et al., 1990, Chem. Rev. 90:543-584; Schneider et al., 1990, Tetrahedron Lett. 31:335).

The isolated nucleic acid of the invention may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size and type of the nucleic acid to be purified and on the characteristics of any molecules, structure, or organisms with which it may be associated. It is furthermore contemplated that the nucleic acid may comprise nucleotide residues other than the five naturally occurring bases, adenine, guanine, thymine, cytosine, and uracil.

Also contemplated is a manufacture comprising a plurality of isolated nucleic acids (i.e. probes) of the invention fixed in an ordered array on a surface. Each of the plurality of probes anneals with high stringency with a portion of the human MCT-1 gene. By including probes which differ by a single nucleotide residue within the corresponding portion of the MCT-1 gene, nucleic acids which comprise different nucleotide residues at that position within the MCT-1 gene may be differentiated. Thus, using methods well known in the art, missense and deletion mutations in the MCT-1 sequence may be detected. Furthermore, by incorporating into the array probes which bind with high affinity with sequential portions of the wild type MCT-1 gene, wherein each sequential portion includes one nucleotide residue not included within the previous sequential portion, the nucleotide sequence of all, or any portion, of the MCT-1 gene may be determined. Preferably, the wild type human MCT-1 cDNA sequence which is used is SEQ ID NO: 7). Manufactures of this type are analogous to the GeneChip™ devices manufactured by Affymetrix, Inc. (Santa Clara, Calif.), which comprise pluralities of primers which bind with high stringency to, for example, portions of the human p53 gene or to portions of the HIV-1 protease or reverse transcriptase genes. Methods for making and using such manufactures have been described elsewhere, and need only be modified by the skilled artisan to include the MCT-1 gene sequences described in the present disclosure (Wallraff et al., February 1997, Chemtech 22-23; Lockhart et al., 1996, Nature Biotechnol. 14:1675-1680; Pease et al., 1994, Proc. Natl. Acad. Sci. USA 91:5022-5026; Fodor et al., 1993, Nature 364:555-556).

The Isolated Polypeptide of the Invention

The invention further relates to an isolated polypeptide which is homologous with at least a portion of MCT-1. The isolated polypeptide of the invention is preferably homologous with at least about ten, fifteen, twenty, or more amino acid residues of SEQ ID NO: 8, which is listed in FIG. 5B. It is understood that SEQ ID NOs: 2 and 8 are identical at amino acid residues 1 to 114. Therefore, these two sequences may be used interchangeably, except that use of SEQ ID NO: 8 is preferred when the identity of one or more of amino acid residues 115 to 181 is critical.

In one embodiment, the isolated polypeptide of the invention comprises amino acid residues 8 to 65 of SEQ ID NO: 8 (or SEQ ID NO: 2). This portion is highly similar to a region of cyclin H protein which has been implicated in protein-protein interactions. Thus, it is recognized that this region of MCT-1 is likely to be at least a significant portion of MCT-1 which interacts with the proteins by means of which MCT-1 exerts its biological effect.

The isolated polypeptide of the invention may have a sequence which comprises all or part of SEQ ID NO: 8. For example, the isolated polypeptide of the invention may be MCT-1 protein, preferably in a substantially purified form. In addition, the sequence of the isolated polypeptide of the invention may further comprise additional amino acid residues (i.e. it may be a fusion protein) or comprise amino acid substitutions, particularly in the random coil portions of MCT-1.

As described herein, MCT-1 has been purified by expressing a GST-MCT-1 fusion protein in an *Escherichia coli* vector and isolating the fusion protein from the vector using known methods. Monoclonal or polyclonal antibodies which bind with specificity to MCT-1 may be generated using known methods and are included in the invention. Antibodies which bind with specificity to MCT-1 are useful for detecting the presence of MCT-1 in a cell, and thus can be used to determine whether a cell is a tumor cell. To determine whether a cell is a tumor cell, an antibody which binds with specificity to MCT-1 is used to detect the presence of MCT-1 in an extract prepared using the cell, using any immunoblotting, immunosorption, or immunoprecipitation technique. The presence of MCT-1 in the cell is an indication that the cell is a tumor cell.

The locations of regions of random coil in the amino acid sequence of MCT-1 may be predicted using standard sequence analysis algorithms (e.g. Garnier-Robson analysis). In random coil regions of proteins, the amino acid sequence is relatively unimportant with regard to the biological activity of the protein. Thus, individual amino acid residues in regions of random coil in SEQ ID NO: 8 may be substituted with substantially any amino acid residue. Other amino acid residues in SEQ ID NO: 8 should only be substituted with conservative amino acid residues. Conservative amino acid residue substitutions are listed on rows of the following table.

TABLE glycine, alanine
valine, isoleucine, leucine
aspartic acid, glutamic acid
asparagine, glutamine
serine, threonine
lysine, arginine
phenylalanine, tyrosine It will be appreciated, of course, that the peptides may incorporate amino acid residues which are modified without affecting biological activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound as an anti-inflammatory agent, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or non-branched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting anti-tumorigenic activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, an isolated polypeptide of the invention may be treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicylic and the like, to provide a water soluble salt of the polypeptide is suitable for use in the methods described herein.

Pharmaceutical Compositions

The invention encompasses the preparation and use of medicaments and pharmaceutical compositions comprising either or both of an isolated nucleic acid of the invention and an isolated polypeptide of the invention as an active ingredient. Such a pharmaceutical composition may consist of the active ingredient(s) alone, in a form suitable for administration to a subject, or the pharmaceutical composition may comprise the active ingredient(s) and one or more pharmaceutically acceptable carriers, one or more additional ingredients, or some combination of these. Administration of one of these pharmaceutical compositions to a subject is useful for preventing or inhibiting tumorigenesis in the subject or for treating a pre-existing tumor, as described elsewhere in the present disclosure. The active ingredient(s) may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient(s) into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient(s), and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient(s). The amount of the active ingredient(s) is generally equal to the dosage of the active ingredient(s) which would be administered to a subject or a convenient fraction of such a dosage such as, for example, one-half or one-third of such a dosage.

The relative amounts of the active ingredient(s), the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient(s).

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient(s). Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water. A tablet comprising the active ingredient(s) may, for example, be made by compressing or molding the active ingredient(s), optionally with one or more additional ingredients. Compressed tablets may be prepared by compressing, in a suitable device, the active ingredient(s) in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient(s), a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient(s). By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient(s) may be made using a physiologically degradable composition, such as gelatin. Such hard capsules comprise the active ingredient(s), and may further comprise additional ingredients including, for example, an inert solid diluent such as calcium carbonate, calcium phosphate, or kaolin.

Soft gelatin capsules comprising the active ingredient(s) may be made using a physiologically degradable composition, such as gelatin. Such soft capsules comprise the active ingredient(s), which may be mixed with water or an oil medium such as peanut oil, liquid paraffin, or olive oil.

Oral compositions may be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663, 308), glycosides (Friend et al., 1984, J. Med. Chem. 27:261-268) and a variety of naturally available and modified polysaccharides (PCT GB 89/00581) may be used in such formulations.

Pulsed release technology such as that described in U.S. Pat. No. 4,777,049 may also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient(s) in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient(s) in aqueous or oily solvents may be prepared in substantially the same manner as liquid suspensions, the primary difference being that the active ingredient(s) is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient(s) in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient(s) with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient(s) with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient(s) with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient(s) combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules, in multi-dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient(s) is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient(s), additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient(s) in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient(s), although the concentration of the active ingredient(s) may be as high as the solubility limit of the active ingredient(s) in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient(s) and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient(s) dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient(s) may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient(s)).

Pharmaceutical compositions of the invention formulated for pulmonary delivery may also provide the active ingredient(s) in the form of droplets of a solution or suspension. Such formulations may be prepared, packaged, or sold as aqueous or dilute alcoholic solutions or suspensions, optionally sterile, comprising the active ingredient(s), and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient(s) and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient(s), and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient(s), the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient(s). Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient(s) in an aqueous or oily liquid carrier. Such drops may further comprise buffering agents, salts, or one or more other of the additional ingredients described herein. Other ophthalmically-administrable formulations which are useful include those which comprise the active ingredient(s) in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

A pharmaceutical composition of the invention may be administered to deliver a dose of between 1 ng/kg/day and 100 mg/kg/day to a subject.

It is understood that the ordinarily skilled physician or veterinarian will readily determine and prescribe an effective amount of the compound to inhibit or treat a tumor in the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the stage of progression of the tumor being treated or inhibited.

Another aspect of the invention relates to a kit comprising a pharmaceutical composition of the invention and an instructional material. As used herein, an "instructional material" includes a publication, a recording, a diagram, or any other medium of expression which is used to communicate the usefulness of the pharmaceutical composition of the invention for inhibiting or treating a tumor in a subject. The instructional material may also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material may be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit may further comprise an instructional material as described herein.

THE METHODS OF THE INVENTION

The invention also relates to a method of reducing MCT-1 expression in a cell. The method comprises providing an isolated nucleic acid of the invention to the cell. Because the isolated nucleic acid is complementary to or homologous with at least about twenty consecutive nucleotides of the mRNA-coding region of an MCT-1 gene to the cell, the nucleic acid anneals with DNA or mRNA in the cell and reduces expression of MCT-1 in the cell. In one embodiment, the isolated nucleic acid is complementary to at least about twenty, and preferably at least about twenty-five, thirty, fifty, or more nucleotide residues of SEQ ID NO: 7, so that the isolated nucleic acid binds with high specificity to mRNA generated by transcription of the genome of the cell and thereby prevents translation of the mRNA, blocking MCT-1 synthesis. The isolated nucleic acid may, for example be complementary to a portion of the mRNA-coding region near or including the translational start site (i.e. nucleotide residues 258-260 of SEQ ID NO: 7). By way of example, the isolated nucleic acid may have a sequence which is 75%, 90%, 95%, or completely complementary to nucleotide residues 240-270 of SEQ ID NO: 7.

The invention also relates to a method of increasing MCT-1 production in a cell. This method comprises providing to the cell an isolated nucleic acid comprising a promoter operably linked with a portion of the mRNA-coding region of a human MCT-1 gene. The region may, for example, include the entire coding sequence of MCT-1 (i.e. nucleotide residues 258-800 of SEQ ID NO: 7), or it may include additional (i.e. a fusion protein) or fewer amino acid residues (i.e. a fragment of MCT-1 such as one including residues 8-65). Of course, the portion of the mRNA-coding region may have amino acid substitutions, as described elsewhere herein. Production of MCT-1 in the cell is increased by expression of the coding sequence of MCT-1 of the isolated nucleic acid. The promoter which is operably linked may be an inducible, suppressible, tissue-specific, or constitutive promoter, each of which is well known in the art.

The invention further relates to a method of determining whether a compound is a modulator of MCT-1 expression. This method of the invention comprises providing a first cell which overexpresses MCT-1, culturing the first cell in the presence of the compound, and comparing MCT-1 expression in the first cell with MCT-1 expression in a second cell of the same type cultured in the absence of the compound. A difference between MCT-1 expression in the first cell and MCT-1 expression in the second cell is an indication that the compound is a modulator of MCT-1 expression. The first cell and the second cell may each be, for example, a leukocyte which has been obtained from a patient afflicted with CTCL and which overexpresses MCT-1.

Expression of MCT-1 in a first cell and in a second cell may be detected and compared using known methods, such as those described herein in the Example. It is understood that this method may also be practiced using a first cell which does not normally express MCT-1 or one which normally expresses MCT-1 at a relatively constant level. When a second cell of the same type is cultured in the presence of a test compound, comparing expression of MCT-1 in the first and second cells will indicate whether the test compound modulates expression of MCT-1. For example, if the first and second cells do not normally express MCT-1, but the second cell expresses MCT-1 in the presence of a test compound, then this is an indication that the test compound is an inducer of MCT-1 expression. The test compound may therefore be considered a potential carcinogen.

The invention also includes a method of determining whether a gene product is a modulator of MCT-1 expression. This method comprises providing a first cell which overexpresses MCT-1, expressing an isolated nucleic acid encoding the gene product in the first cell, and comparing MCT-1 expression in the first cell with MCT-1 expression in a second cell of the same type, wherein the isolated nucleic acid is not expressed in the second cell. A difference between MCT-1 expression in the first cell and MCT-1 expression in the second cell is an indication that the gene product is a modulator of MCT-1 expression. It is understood that this method may also be practiced using a first cell which does not normally express MCT-1 or one which normally expresses MCT-1 at a relatively constant level.

The invention further includes a method of determining whether a cell is a tumor cell. This method of the invention comprises comparing MCT-1 expression in the cell and MCT-1 expression in a non-tumor cell, preferably of the same type (e.g. by comparing MCT-1 expression in a T-cell suspected of being cancerous and in a T-cell not suspected of being cancerous). A difference between MCT-1 expression in the cell and MCT-1 expression in the non-tumor cell is an indication that the cell is a tumor cell. The method can be used, for example, to determine whether the cell is a cutaneous T-cell lymphoma cell. The non-tumor cell may, for example, be a normal human lymphocyte.

The invention includes another method of determining whether a cell is a tumor cell. This alternate method comprises comparing MCT-1 copy number in the cell and MCT-1 copy number in a non-tumor cell. A difference between MCT-1 copy number in the cell and MCT-1 copy number in the non-tumor cell is an indication that the cell is a tumor cell. The method can be used, for example, to determine whether the cell is a cutaneous T-cell lymphoma cell. The non-tumor cell may, for example, be a normal human lymphocyte. The copy number of MCT-1 in a first cell and in a second cell may be detected and compared using known methods, such as those described herein in the Example.

The invention also relates to a method of conferring a growth advantage on a cell. This method comprises providing the cell with an isolated nucleic acid comprising a promoter operably linked to a portion of the mRNA-coding region of an MCT-1 gene, the region including the coding sequence of MCT-1 (i.e. nucleotide residues 258-623 of SEQ ID NO: 1). By providing this isolated nucleic acid to the cell, MCT-1 expression is enhanced, as described in the Example, and a growth advantage is conferred upon the cells, relative to cells not provided the isolated nucleic acid.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Molecular Cloning and Characterization of a Novel Gene, MCT-1, which is Amplified in a Cutaneous T-Cell Lymphoma Cell Line The experiments presented in this Example demonstrate that overexpression of MCT-1 protein in NIH 3T3 fibroblasts shortens the G1 phase of the cell cycle and promotes anchorage independent growth.

Genetic abnormalities of malignant T-cells associated with cutaneous T-cell leukemia (CTCL) were identified using arbitrarily primed-polymerase chain reaction (AP-PCR) assay. AP-PCR has been used by others to detect sub-microscopic genetic alterations which are associated with tumorigenesis, as described (Welsh et al., 1990, Nucl. Acids Res. 18:7213-7218; Peinado et al., 1992, Proc. Natl. Acad. Sci. USA 89:10065-10069; Kohno et al., 1993, Oncogene 7:103-108).

A panel of T-cell leukemia and lymphoma cell lines was screened for amplified genomic sequences. An amplified genomic sequence was identified in a cell line designated HUT 78. This genomic sequence was cloned and sequenced, and the coding sequence encoded by the genomic sequence was determined to have no significant homology to any known gene sequence in the BLAST genome data base, as determined using the Basic Local Alignment Search Tool. It was therefore concluded that the amplified genomic sequence comprised at least part of a novel gene.

The novel gene was designated MCT-1 (multiple copies in T-cell malignancies). The amplified genomic sequence encoded a polypeptide of 181 amino acids (SEQ ID NO: 8), designated MCT-1. The MotifFinder computer program was used to identify three putative post-translational modification sites in MCT-1, as indicated in FIG. 3. PCR primers were designed using the MacVector program, and these primers were used to generate a 457 nucleotide residue amplification product when genomic DNA was subjected to PCR. The primers which were used were designated HuT 78F, which had the nucleotide sequence 5'-CATTGGAGAC CGCTACA-CAC AGGAC-3' (SEQ ID NO: 3), and HuT 78R, which had the nucleotide sequence 5'-CTGTCAAAAT AGTCCGATGC CACG-3' (SEQ ID NO: 4). The same primers were also useful for amplifying cDNA in an RT-PCR assay, confirming that the amplified band obtained during the AP-PCR assay was an exon.

Northern blot analysis revealed ubiquitous low-level expression of a 943 nucleotide residue MCT-1 message in normal human tissues. The full length cDNA sequence corresponding to the MCT-1 message (hereinafter, "the MCT-1 cDNA") was determined using a rapid amplification of cDNA ends (RACE) method, as described (Frohman, 1993, Meth. Enzymol. 218:340-356). The nucleotide sequence (SEQ ID NO: 7) of the MCT-1 cDNA is listed in FIG. 5A, and the amino acid sequence (SEQ ID NO: 8) of the 181-amino acid residue polypeptide encoded thereby is listed in FIG. 5B.

Figures 1A, 1B:
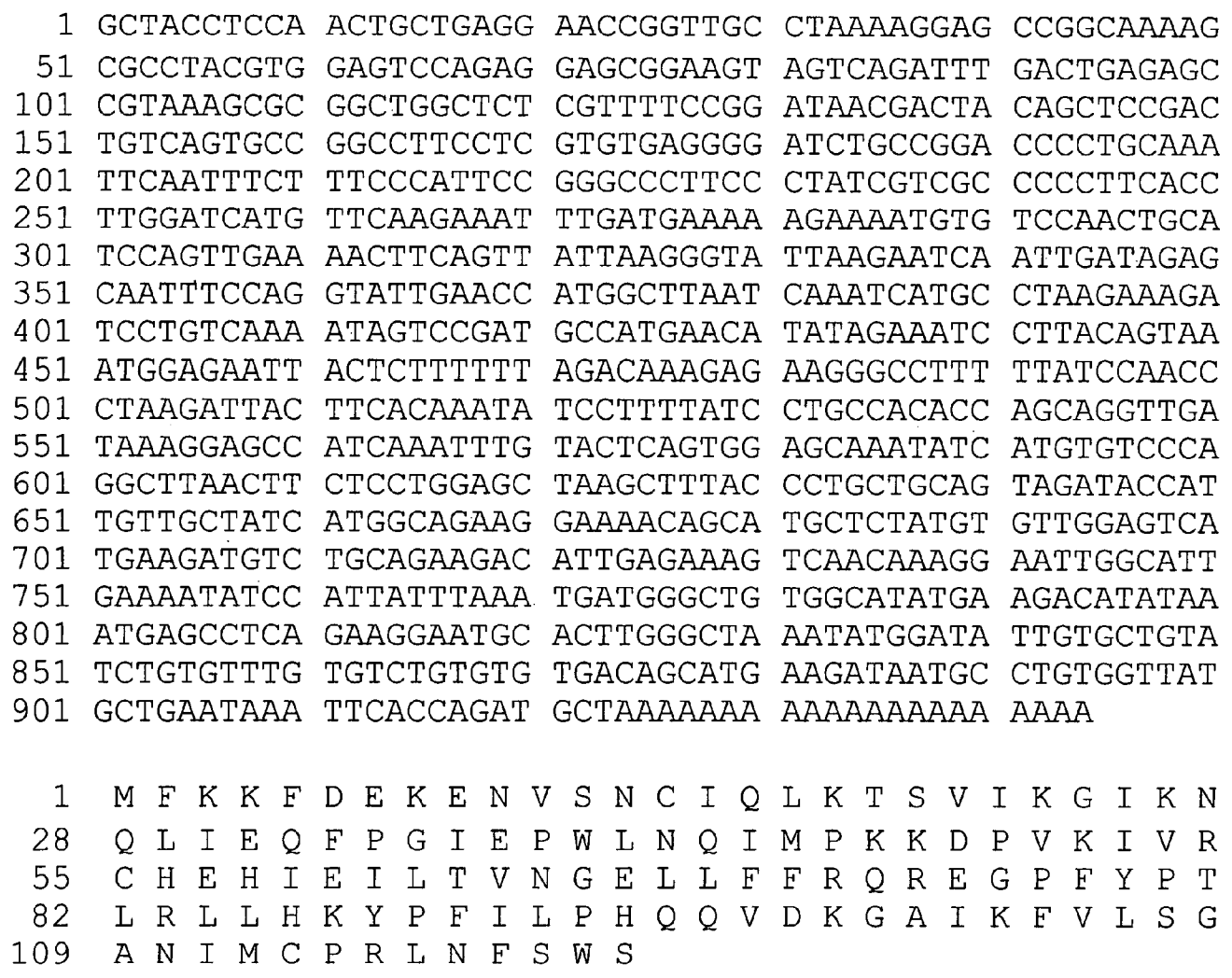

Due to a sequencing error, the nucleotide sequence was initially believed to comprise an additional cytosine residue located between the cytosine residue at position 598 and the adenine residue a position 599, as indicated in the sequence listed in FIG. 1A (SEQ ID NO: 1). The putative amino acid sequence (SEQ ID NO: 2) encoded by the erroneous sequence is listed in FIG. 1A, and differs from the amino acid sequence of MCT-1 at amino acid residues 115 to 181.

The dbEST database was compared with the sequence of the MCT-1 cDNA, and several overlapping ESTs having homology therewith were identified. These overlapping regions are indicated in FIG. 2. MCT-1 was localized to the long arm of chromosome Xq22-24 using bacterial artificial chromosome (BAC) clones which contained either the 5'-region, the 3'-region, or both regions of the MCT-1 cDNA.

Although there was no significant homology between MCT-1 and any known protein at the primary sequence level, there was one interesting alignment at the structural protein level, as assessed using the NRL-3D Database (Amino Acid Sequence Extraction, Brookhaven Structural Database). A potentially important region (SEQ ID NO: 9) of MCT-1 is the amino terminal half of the protein, which has a sequence identity of 32% with a 58-amino-acid-residue domain (SEQ ID NO: 10) of cyclin H, as indicated in FIG. 4. It is understood that proteins of the immunoglobulin superfamily have only, on average, about 23% sequence identity. It is known from crystallographic studies that the basic three dimensional folding patterns among this superfamily of proteins is extremely well conserved.

The region of homology between MCT-1 and cyclin H covers a region of cyclin H that spans a surface domain of the protein that is putatively involved in protein-protein interactions (Andersen et al., 1997, EMBO J. 16:958-967). The non-homologous regions of MCT-1 and cyclin H correspond to regions of random coil within the cyclin H molecule. Therefore, MCT-1 may be predicted to exhibit high structural homology with cyclin H. Thus, the homologous region of MCT-1 may also be involved in protein-protein interactions, and MCT-1 was hypothesized to have a role in cell cycle regulation.

In order to test this hypothesis, MCT-1 was overexpressed in NIH 3T3 fibroblasts, and the effect on growth of those cells was observed. Following transfection of the fibroblasts, an approximately two-fold decrease in the duration of the G1/S phase of the cell cycle was observed, relative to non-transfected fibroblasts. Over expression of MCT-1 increases the proliferative rate of cells by decreasing the length of G1 phase without causing a reciprocal increase in the durations of the S or G2-M phases.

The transforming ability of MCT-1 was assessed by soft agar growth assays. Soft agar culture assays were performed essentially as described (Hsiao et al., 1989, Mol. Cell. Biol. 9:2641-2647). Using limiting dilution, clonal cell lines of pcDNA3 and pCMV-MCT-1-transfected cells were established. Briefly, NIH 3T3 fibroblast monolayers transfected with pcDNA3 or pCMV-MCT-1 were seeded into 0.3% (w/v) Bacto-Agar suspension supplemented with DMEM and 20% (v/v) fetal calf serum. This suspension was overlaid above a layer of 0.5% (w/v) agar in the same medium on a 90 millimeter diameter plate. Samples were made in triplicate and re-fed every four days. Colonies were scored both by naked eye and by microscopy. Neither the parent cell line nor cells transfected with pCMV proliferated. Growth of pCMV-MCT-1-transfected cells was observed after four weeks. Thus, it was demonstrated that only MCT-1-overexpressing cells remained viable and continued to proliferate Some cell cycle regulatory proteins are directly involved in oncogenesis, and cyclins have specifically been implicated in tumorigenesis. Amplification of cyclin E has been demonstrated in both breast and colon cancer cell lines (Keyomarsi et al., 1993, Proc. Natl. Acad. Sci. USA 90:1112-1116; Leach et al., 1993, Cancer Res. 53:1986-1989). The strongest evidence to date for participation of cyclins in oncogenesis it that cyclin D1 amplification and overexpression occurs in primary human breast tumors (Buckley et al., 1993, Oncogene 8:2127-2133) and that cyclin D1 overexpression leads to transformation in vitro (Jiang et al., 1993, Oncogene 8:3447-3457). Furthermore, a D-type cyclin, CCND2, has been implicated in cell cycle progression, and has recently been demonstrated to be amplified in non-Hodgkin's lymphoma (Sherr, 1993, Cell 73:1059-1065; Hoglund et al., 1996, Blood 87:324-330).

The HUT 78 cell line in which MCT-1 amplification was observed was derived from peripheral blood cells obtained from a patient afflicted with Sezary syndrome. Because MCT-1 was localized to chromosomal bands Xq22-24, primary samples from patients afflicted with either CTCL (n=40) or chronic lymphocytic leukemia (n=20). Amplification of MCT-1 was not detected in these samples. Nonetheless, it appears that MCT-1 overexpression contributes to deregulated cell cycle progression and proliferation in vitro. Further support for the hypothesis that MCT-1 is an oncogene is provided by the observation that the gene supports soft agar growth in fibroblasts which over express it and by the observed structural homology between MCT-1 and cyclin H.

The materials and methods used in the experiments presented in this Example are now described.

Chromosomal localization of MCT-1 was ascertained by fluorescent in situ hybridization (FISH) analysis. Briefly, a BAC library was screened using PCR primers homologous with or complementary to the 5'- and 3'-ends of the cDNA listed herein in FIG. 1A (SEQ ID NO: 1). Two BAC clones (BAC 5839 and BAC 5841) hybridized with both the 5'- and the 3'-primer. Each BAC probe was labeled with dioxigenin dUTP by nick translation. The labeled probe was hybridized to normal metaphase chromosomes from phytohemagglutinin-stimulated peripheral blood lymphocytes. Specific hybridization signals were observed on the long arm of the X chromosome (Xq22-24) using BAC 5839.

Stable cell lines which overexpressed human MCT-1 were established by transfecting NIH 3T3 fibroblasts either with vector pcDNA3 (comprising promoter pCMV) alone or with vector comprising the full length MCT-1 cDNA (pCMV-MCT-1). Geneticin (G418) resistance was conferred by pCMV-MCT-1. pCMV-MCT-1 was made using specific restriction enzymes. To generate pCMV-MCT-1, the vector comprised the T7 promoter operably linked to the coding sequence of MCT-1 was generated using primers having nucleotide sequences (+) 5'-GCTGAGGATC CGGTTGC-CTA AAAG-3' (SEQ ID NO: 5) and (−) 5'-TCTGGTGAAT TCATTCAGCA TAA-3' (SEQ ID NO: 6), digested with BamHI and EcoRI, and ligated to pCMV. These constructs were verified by DNA sequence analysis.

Transfected cells were grown in selection medium for 2 weeks. Selection medium comprised Dulbecco's modified Eagle's medium (DMEM) complete plus 1 milligram per milliliter G418. In this medium, 100% of mock transfected cells exhibited cell death. Controls included cells transfected with vector (pcDNA3) alone and non-transfected 3T3. Population doubling times were calculated by counting cells every 72 hours for 12 days.

After serum depletion for 48 hours, cells were re-plated at $3 \times 10^5$ cells per 10-centimeter diameter dish in DMEM plus 10% (v/v) fetal calf serum (FCS). Every two hours cells were collected and analyzed for DNA content by flow cytometry. Fluorescence data was collected using an Epics Coulter flow cytometer, and the percentage of cells in each of the G1, S, and G2-M phases of the cell cycle were determined by analysis with the software program, MultiCycle (Phoenix).

AP-PCR

Genomic DNA was prepared from all T-cell lines and normal PBL samples. All reactions were carried out in a 25 microliter volume containing 10 millimolar Tris-HCl, 200 millimolar each dNTP, 50 millimolar KCl, 5 millimolar $MgCl_2$, 25 picomoles of 10-mer arbitrary primer, 0.1 milligram DNA template and 1 Unit Taq DNA Polymerase (Fisher Biotech) at pH 8.3. A panel of 10-mer to 20-mer primers were labeled using T4 polynucleotide kinase and $[\gamma^{32}P]$-ATP. All reactions were performed using a GeneAMP PCR System 9600 (Perkin-Elmer). The profile was as follows. The first 5 cycles of the temperature profile:

denaturation at 95° C. for 30 seconds, then
primer annealing at 25° C. for 1 minute, and then
extension for 1 minute at 72° C.

The last 25 cycles:

denaturation at 95° C. for 30 seconds, then
primer annealing at 30° C. for 30 seconds, and then
extension for 1 minute at 72° C.

PCR products were separated by electrophoresis in denaturing 8 molar urea/polyacrylamide gels followed by autoradiography.

Cloning and Sequencing of Genomic MCT-1 Sequences Amplified by AP-PCR

The band that appeared to be amplified in the HUT 78 lane relative to the corresponding bands from other cell lines and normal lymphocytes was isolated for cloning and sequencing. This band was excised from gels and incubated in 10 milliliters of 1× Assay Buffer A (Fisher Biotech catalog no. FB6000-10) at 90° C. for 10 minutes. Five microliter of eluted DNA was re-amplified using the same AP-PCR primer as before with $MgCl_2$ concentration of 5 millimolar for 30 cycles at 30° C. The PCR product was analyzed by electrophoresis in a polyacrylamide gel to confirm its size and purity. Amplified DNA was cloned into a compatible thymidine pMOSBlue T-vector (Amersham, Arlington Heights, Ill.). The presence of an appropriate insert was determined using direct colony PCR using T7 and U19-mer pMOSBlue specific primers. Sequencing was performed using an established methodology. Sequences obtained from several clones was compared to known sequences in the GenBank data base using the BLASTn and BLASTx computer programs (Altschul et al., 1990, J. Mol. Biol. 215:403-410).

Isolation and Sequencing of MCT-1 cDNA

Full length MCT-1 cDNA sequence was obtained by the RACE method as previously described using normal peripheral blood lymphocyte (PBL) cDNA (Frohman, 1993, Meth. Enzymol. 218:340-356).

Southern Blot Analysis

5 To 10 micrograms of genomic DNA of cells obtained from humans afflicted with CTCL or CLL was digested with either HindIII or EcoRI and electrophoresed in 1.0% (w/v) agarose gels. Transfer to nitrocellulose membrane and subsequent hybridization was performed using standard methods. An MCT-1 cDNA probe was random primed with PRIME-IT kit (Stratagene, La Jolla, Calif.) and purified using PrimeErase Quik columns (Stratagene) according to the supplier's directions. The occurrence of gene amplification was assessed by comparing the ratio of MCT-1 to β-actin signals. Quantification was carried out using a STORM phosphorimager 860 (Molecular Dynamics, Sunnyvale, Calif.).

Example 2

Increased G1 Cyclin/cdk Activity in Cells Overexpressing MCT-1

The materials and methods used in the experiments presented in this Example are now described.

NIH 3T3 Cell Culture and DNA Transfection

Stably transfected NIH 3T3 cell lines which constitutively expressed MCT-1 (i.e. which comprised plasmid pCMV-MCT-1) and stably transfected cell lines which comprised a control (pCMV) vector were generated as described in Example 1. Individual clones of transfected cells were obtained by limiting dilution.

Transient assays of the level of MCT-1 protein expression were performed using the Lipofectamine method according to the supplier's instructions (GIBCO, Grand Island, N.Y.). Briefly, an expression vector (pcDNA-HA-MCT-1, which encodes a protein having an HA tag fused at the amino terminus of MCT-1) was constructed by cloning cDNA encoding MCT-1 into BamHI and EcoRI site of pcDNA3-HA. Transfected cells were analyzed 48 hours later for production of the fusion protein HA-MCT-1 using an anti-HA antibody described herein.

Lymphocyte Cell Lines

PBL (peripheral blood lymphocytes) were prepared from whole fresh blood of healthy donors. Mononuclear cells were isolated by centrifugation in the presence of Ficoll (Organon Teknika Corporation, Durham, N.C.), cultured for 48 hours in RPMI 1640 medium containing 20% (v/v) FCS, 100 Units per milliliter penicillin, 100 micrograms per milliliter streptomycin, 2 millimolar L-glutamine, and 1% (w/v) phytohemagglutinin (PHA; GIBCO, Grand Island, N.Y.). Non-adherent PBL were viably frozen for further analysis.

Interleukin-2-(IL-2-) independent cell lines which were used included cell lines C10MJ, MT-2, Hut 78, H-9, HUT 102, DA 202, and C91PL (Advanced Biotechnologies Inc., Columbia, Md.). Cells of these lines were cultured in RPMI 1640 medium containing 10% FCS, 100 Units per milliliter penicillin, 100 micrograms per milliliter streptomycin and 2 millimolar glutamine (GIBCO, Grand Island, N.Y.). IL-2-dependent cell lines N1185 and N1186 (described by Berneman et al., 1992, Proc. Natl. Acad. Sci. USA 89:3005-3009) were cultured using the same culture conditions as above with the addition to the medium of 40 Units per milliliter of recombinant IL-2 (GIBCO, Grand Island, N.Y.).

Immunoprecipitation and Immunoblotting

Cell pellets were lysed in lysate buffer, which comprised 10 millimolar Tris, 150 millimolar NaCl, 1 millimolar EDTA, 0.1% (w/v) SDS, and 150 millimolar phenylmethylsulfonyl fluoride (PMSF) at a pH of 7.4. Total protein concentration in each sample was determined using a commercial bicinchoninic acid assay kit (micro-BCA™ kit; Pierce, Rockford, Ill.) according to the manufacturer's instructions. Equal amounts of whole cell lysate (50 to 100 micrograms) were resuspended in 5 milliliters of TBS containing (final concentrations) 1 microgram per milliliter leupeptin, 1 microgram per milliliter aprotinin, 0.01% (w/v) PMSF, 0.01% (w/v) n-tosyl-L-phenylalanine-chloromethyl ketone (TPCK), 0.01% (w/v) n-alpha-p-tosyl-L-lysine-chloromethyl ketone (TLCK), 0.1% (w/v) sodium azide and 1% (w/v) nonyl phenoxy polyethoxy ethanol (NP-40; SIGMA, Saint Louis, Mo.). TBS was Tris-buffered saline containing 0.1% (w/v) sodium dodecyl sulfate. Samples were pre-cleared with Protein-G beads (GIBCO, Grand Island, N.Y.) and either normal rabbit or mouse serum (each at a 1:1000 dilution). Immunoprecipitation of cyclin D1 was carried out for 12 hours at 4° C. Immune complexes were precipitated using 1 to 5 micrograms of antibody and Protein-G agarose, and were then heated at 95° C. for 5 minutes in IP buffer, which comprised 93 millimolar Tris, 3% (w/v) SDS, 1.1 millimolar β-mercaptoethanol, 0.03% (w/v) bromophenol blue (BPB), and 15% (v/v) glycerol (SIGMA, Saint Louis, Mo.) at a pH of 6.8. The eluant was analyzed using a denaturing, reducing SDS-PAGE gel, and the contents of the gel were transferred to supported nitrocellulose filter by electroblotting. Filters were incubated with 1 to 5 micrograms of an antibody which binds specifically with one of the following: cyclin D1, cdk4, cdk6, PCNA, and p21. Horseradish peroxidase-linked anti-mouse or anti-rabbit whole antibody was used as a secondary antibody. Chemiluminescence was detected using an ECL™ kit (Amersham Life Science, Arlington Heights, Ill.) according to the manufacturer's instruction.

Immune Complex Protein Kinase (CDK4 and CDK6) Assays

NIH 3T3 cell pellets were lysed in lysate buffer. Total protein concentration in each sample was determined using the micro BCA™ kit (Pierce, Rockford, Ill.) according to the manufacturer's instructions. 50 Microgram aliquots of cell extract were transferred to individual microfuge tubes, and the total volume was brought to 500 microliters with IP buffer. Immunoprecipitation was performed by incubating these solutions overnight at 4° C. in the presence of 2.5 micrograms of mouse monoclonal anti-cdk4 antibody or anti-cdk6 antibody, followed by incubation for 4 hours in the presence of 25 microliters of protein G-agarose beads. This amount of beads provided an excess of G-agarose, relative to antibody. Precipitated protein pellets were washed 3 times using ice-cold lysate buffer and then resuspended in 20 milliliters of ice-cold kinase buffer, which comprised 50 millimolar HEPES buffer, 80 millimolar β-glycerophosphate, 2.5 millimolar ethylene glycol bis(β-aminoethyl ether)-N,N,N', N'-tetraacetic acid (EGTA), 10 millimolar $MgCl_2$, 1 millimolar dithiothreitol (DTT), 2.5 millimolar PMSF, 60 KIU per milliliter aprotinin, 10 milligrams per milliliter leupeptin, and 10 millimolar cyclin AMP-dependent protein kinase-inhibitory peptide (SIGMA, Saint Louis, Mo.) at a pH of 7.5. 12 Milliliters of a reaction mix which comprised 10 microcuries of $\gamma[-^{32}P]ATP$ (about 3,000 Curies per millimole; Amersham, Arlington Heights, Ill.), 25 millimolar non-labeled ATP, and 200 nanograms of Rb protein as substrate were added to each sample, and the mixed samples were incubated at 30° C. for 15 minutes. GST-RB was expressed and purified as previously described (Meyerson and Harlow, 1994) as a source of Rb protein for the reaction mix. Kinase reactions were stopped by adding a volume of 2×SDS sample buffer equal to the volume of the mixed sample and boiling this diluted sample for 5 minutes. 2×SDS sample buffer comprised 4% (w/v) SDS, 150 millimolar Tris chloride, 20% (v/v) glycerol, 0.02% (w/v) BPB, and 2 millimolar sodium vanadate at a pH of 6.8. Proteins in the boiled, diluted sample were separated by SDS-PAGE in a 10% (w/v) gel. After drying, the gel was assayed by autoradiography to detect labeled proteins.

Antibodies

Monoclonal and polyclonal antibodies designated HD11 (anti-cyclin D1), PC10 (anti-PCNA), F-5 (anti-p21), H-303 (anti-cdk4), and H-230 (anti-cdk6) were obtained from Santa Cruz Biotechnology (Santa Cruz, Calif.). Polyclonal MCT-1 antibodies were generated by inoculating rabbits with a synthetic peptide corresponding to the first 20 amino acids at the amino terminus of MCT-1. Immune sera was provided by Research Genetics (Huntsville, Ala.).

Western Blot

Cultured cells ($5 \times 10^6$ to $10 \times 10^6$) were washed three times with phosphate buffered saline (PBS). Cells were collected by centrifugation, and the pellet was lysed in lysate buffer. The total protein concentration in each sample was determined using the micro BCA™ kit (Pierce, Rockford, Ill.) according to the manufacturer's instructions. 25 Micrograms of total protein per sample was fractionated by electrophoresis in a Tris-glycine PAGE gel (Novex, San Diego, Calif.) under denaturing, reducing conditions. The proteins in the gel were transferred to supported nitrocellulose filters using an electroblotting apparatus (Millipore, Marlborough, Mass.). Replicate filters were incubated either with anti-cyclin D1 antibody or with MCT-1 immune sera. Chemiluminescence was performed using an ECL™ kit (Amersham Life Science, Arlington Heights, Ill.) according to the manufacturer's instruction. The filters were then exposed to x-ray film and labeled proteins were quantitated by laser densitometry using a personal densitometer (Molecular Dynamics, Sunnyvale, Calif.).

Focus Forming Assay

Stable transfectants and cells of the parent cell lines were grown to near confluence, and were then plated in 100-millimeter tissue culture dishes at a density of about $0.5 \times 10^6$ cells per dish. The cultures were re-fed every 5 to 6 days, and the number of transformed foci was determined after 2 weeks. Focus formation and morphologic changes were visualized both by the naked eye and by microscopy after incubation for 1 hour with Coomassie blue. All experiments were reproduced at least three times for each DNA transfected.

The results of the experiments presented in this Example are now described. These experiments were designed to examine the impact of MCT-1 overexpression on protein kinase-mediated G1 phase checkpoints. The kinase activity of two cyclin D1-associated cdks, cdk4 and cdk6, was examined in NIH 3T3 cells which constitutively expressed MCT-1. The cellular levels of cyclin D1 protein, and the association of cyclin D1 with cdk4, cdk6, PCNA, and p21 were also assessed.

Steady state cellular protein levels of MCT-1 in NIH 3T3 cells stably transfected with pCMV-MCT-1 or with control vector (pCMV), as well as non-transfected 3T3 cells, were assessed by Western blot analysis. An approximately 20 kilodalton band was detected with a greater intensity in cell lysates obtained from cells transfected with pCMV-MCT-1 than in lysates obtained from non- or control-transfected cells. Similar results were obtained using a transient transfection assay involving HA-tagged MCT-1 protein. HA-tagged MCT-1 protein could be immunoprecipitated from lysates of cells transfected with pCMV-HA-MCT-1, and HA-tagged MCT-1 was detected by Western blotting at a position corresponding to a size of about 20 kilodaltons.

An increased level of cyclin D1 protein was detected by immunoprecipitation in lysates from NIH 3T3 cells transfected with PCMV-MCT-1, relative to asynchronously grown control cells which were not transfected or which were transfected with control vector. Because cdk4 and cdk6 associate with cyclin D1 during cell cycle progression, complex formation among these molecules was investigated using co-immunoprecipitation analysis. Increased subunit complex formation in NIH 3T3 cells constitutively expressing MCT-1, relative to cells which were not transfected with a vector encoding MCT-1. Physical interaction of PCNA with cyclin D1-cdk4/cdk6 complexes was also investigated. Co-immunoprecipitation of cyclin D1 and PCNA was detected at an increased level, relative to cells which were not transfected with a vector encoding MCT-1. Direct physical interaction was not detected between MCT-1 and any of proteins cyclin D1, cdk4, cdk6, and PCNA under these assay conditions.

Previous studies demonstrated that ectopic expression of cyclin D1 can induce transcriptional activation of the p21 gene (Hiyama et al., 1997, Oncogene 14: 2533-2542). In normal human fibroblasts, the cdk inhibitory protein p21 can be detected in association with various cyclin/cdk complexes in combination with PCNA (Zhang et al., 1993, Mol. Biol. Cell 4:897-906). Therefore, these G1 cyclin/cdk complexes were examined for the presence p21. Protein p21 was determined to be associated with these complexes in cell lines which constitutively expressed MCT-1.

Previous studies establish that p21 can act as a universal inhibitor of cyclin/cdk kinase activity (Xiong et al., 1993, Nature 366:701-704). Because increased G1 cyclin/cdk complexes were observed in cells which overexpressed MCT-1, as described in this Example, we analyzed the catalytic activity of cdk4 and cdk6 in extracts made from these cells were assessed. A markedly increased ability to phosphorylate Rb protein (a substrate of both cdk4 and cdk6) was observed in in vitro immune complex kinase assays performed using either cdk4 or cdk6 immunoprecipitated from MCT-1-overexpressing cells. Without wishing to be bound by any particular theory of operation, these data suggest that association of a single p21 molecule with a cyclin/cdk complex permit stables complex formation among cyclin D1, cdk and PCNA.

Using a focus forming assay, the ability of cells overexpressing MCT-1 to form foci comprising smaller cells that grew in clusters was demonstrated. Focus formation could not be detected among non- or control-transfected cells. These results are consistent with earlier work showing that fibroblasts overexpressing cyclin D1 exhibit morphological changes and grow in clusters (Jiang et al., 1993, Oncogene 8:3447-3457; Wang et al., 1994, Nature 369:669-671).

MCT-1 and cyclin D1 protein levels were assessed in asynchronously-grown T-cell tumor cells and PBL control cells. A number of the T-cell tumor cell lines exhibited elevated MCT-1 protein levels relative to PBL controls. Increased MCT-1 protein expression correlated with increased levels of cyclin D1. The two IL-2 dependent cell lines N1185 and N1186 exhibited increased levels of cyclin D1, but contained no detectable MCT-1 protein. The HUT 78 cell line had the highest level of MCT-1 protein. This result is consistent with gene amplification as described in Example 1 herein. None of the other tumor cell lines analyzed in this study exhibited MCT-1 gene amplification.

A striking finding of the experiments described in this Example is the strong correlation between MCT-1 overexpression and elevated cyclin D1 protein levels, both in transfected NIH 3T3 cells and in a panel of T-cell tumor cell lines. These experiments demonstrate for the first time that MCT-1 protein is endogenously expressed in tumor cells. Furthermore, these experiments also highlight the biological significance of genomic amplification of MCT-1 in the HUT 78 cell line, since the level of MCT-1 protein is greatly increased relative to the other cell lines which do not exhibit genomic amplification.

Without wishing to be bound by any particular theory of operation, it is recognized that these data are consistent with MCT-1 acting through an upstream mechanism(s) involving cyclin D1 resulting in dys-regulation of G1-associated cdk activity. MCT-1 overexpression induces cells to pass through cell cycle phase G1. It has been demonstrated by others that when cyclin D1 levels are elevated, as they are in cells constitutively expressing MCT-1 (as described herein), expression of several genes involved in growth regulation are induced (Jiang et al., 1993, Oncogene 8:3447-3457). Furthermore, the amino terminus of MCT-1 shares a region of homology with the carboxyl terminal region of cyclin H. As described in Example 1, this region of cyclin H is known to be involved in protein-protein interactions (Andersen et al., 1997, EMBO J. 16:958-967). Cyclin H forms a ternary complex with proteins cdk7 and MAT 1, and together these proteins form the cdk-activating kinase (CAK). The CAK is responsible for activating cdk1, cdk2 and cdk4 (Nigg, 1996, Curr. Opin. Cell Biol. 8:312-317).

Thus, still not wishing to be bound by any particular theory of operation, a plausible explanation for the rapid progression of MCT-1 overexpressing cells through the G1 phase is enhancement of CAK activity and increased cyclin D1 protein expression, which is coupled with enhanced expression of other growth regulating genes. The experiments described in this Example demonstrate that overexpression of MCT-1 results in loss of normal cell cycle regulatory controls with an increase in G1 cyclin/cdk complex formation. While the underlying mechanisms are not known at present, dys-regulation of MCT-1 appears to be a potent transforming event in vitro, and overexpression is increased in T-cell tumor cell lines relative to normal lymphocytes. These observations demonstrate that abnormally high levels of expression of MCT-1 protein can be used as an indicator of the tumor state of a cell, and that tumorigenesis may be inhibited by inhibiting expression of MCT-1, such as by providing an antisense oligonucleotide which is complementary to or homologous with a portion of the gene encoding MCT-1 to a cell.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising isolated polyclonal antibodies which bind with specificity to a protein comprising the sequence of SEQ ID NO:8.

\* \* \* \* \*

SEQUENCE LISTING

```
<160> NUMBER OF SEQ ID NOS: 10

<210> SEQ ID NO 1
<211> LENGTH: 944
<212> TYPE: DNA
<213> ORGANISM: Homo sapiens
<220> FEATURE:
<223> OTHER INFORMATION: Human cDNA

<400> SEQUENCE: 1
gctacctcca actgctgagg aaccggttgc ctaaaaggag ccggcaaaag cgcctacgtg      60
gagtccagag gagcggaagt agtcagattt gactgagagc cgtaaagcgc ggctggctct    120
cgttttccgg ataacgacta cagctccgac tgtcagtgcc ggccttcctc gtgtgagggg    180
atctgccgga cccctgcaaa ttcaatttct ttcccattcc gggcccttcc ctatcgtcgc    240 cccccttcacc ttggatcatg ttcaagaaat ttgatgaaaa agaaaatgtg tccaactgca    300
```

-continued

```
tccagttgaa aacttcagtt attaagggta ttaagaatca attgatagag caatttccag    360
gtattgaacc atggcttaat caaatcatgc ctaagaaaga tcctgtcaaa atagtccgat    420
gccatgaaca tatagaaatc cttacagtaa atggagaatt actcttttt agacaaagag     480 aagggccttt ttatccaacc ctaagattac ttcacaaata tccttttatc ctgccacacc    540
agcaggttga taaggagcc atcaaatttg tactcagtgg agcaaatatc atgtgtccca     600
ggcttaactt ctcctggagc taagctttac cctgctgcag tagataccat tgttgctatc    660
atggcagaag gaaaacagca tgctctatgt gttggagtca tgaagatgtc tgcagaagac    720
attgagaaag tcaacaaagg aattggcatt gaaaatatcc attatttaaa tgatgggctg    780
tggcatatga agacatataa atgagcctca gaaggaatgc acttgggcta aatatggata    840
ttgtgctgta tctgtgtttg tgtctgtgtg tgacagcatg aagataatgc ctgtggttat    900
gctgaataaa ttcaccagat gctaaaaaaa aaaaaaaaa aaaa                       944
```

```
<210> SEQ ID NO 2
<211> LENGTH: 121
<212> TYPE: PRT
<213> ORGANISM: Homo sapiens
<220> FEATURE:
<223> OTHER INFORMATION: Putative sequence of protein encoded by human
      cDNA of SEQ ID NO: 1

<400> SEQUENCE: 2

Met Phe Lys Lys Phe Asp Glu Lys Glu Asn Val Ser Asn Cys Ile Gln
 1               5                   10                  15

Leu Lys Thr Ser Val Ile Lys Gly Ile Lys Asn Gln Leu Ile Glu Gln
                20                  25                  30

Phe Pro Gly Ile Glu Pro Trp Leu Asn Gln Ile Met Pro Lys Lys Asp
            35                  40                  45

Pro Val Lys Ile Val Arg Cys His Glu His Ile Glu Ile Leu Thr Val
        50                  55                  60

Asn Gly Glu Leu Leu Phe Phe Arg Gln Arg Glu Gly Pro Phe Tyr Pro
 65                  70                  75                  80

Thr Leu Arg Leu Leu His Lys Tyr Pro Phe Ile Leu Pro His Gln Gln
                85                  90                  95

Val Asp Lys Gly Ala Ile Lys Phe Val Leu Ser Gly Ala Asn Ile Met
            100                 105                 110

Cys Pro Arg Leu Asn Phe Ser Trp Ser
        115                 120

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer HuT
      78F

<400> SEQUENCE: 3
cattggagac cgctacacac aggac                                            25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer HuT
      78R
```

```
<400> SEQUENCE: 4
ctgtcaaaat agtccgatgc cacg                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: pCMV-MCT-1
      Generation Primer (+)

<400> SEQUENCE: 5
gctgaggatc cggttgccta aaag                                          24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: pCMV-MCT-1
      Generation Primer (-)

<400> SEQUENCE: 6
tctggtgaat tcattcagca taa                                           23

<210> SEQ ID NO 7
<211> LENGTH: 943
<212> TYPE: DNA
<213> ORGANISM: Homo sapiens
<220> FEATURE:
<223> OTHER INFORMATION: cDNA encoding MCT-1

<400> SEQUENCE: 7
gctacctcca actgctgagg aaccggttgc ctaaaaggag ccggcaaaag cgcctacgtg    60
gagtccagag gagcggaagt agtcagattt gactgagagc cgtaaagcgc ggctggctct   120
cgttttccgg ataacgacta cagctccgac tgtcagtgcc ggccttcctc gtgtgagggg   180
atctgccgga cccctgcaaa ttcaatttct ttcccattcc gggcccttcc ctatcgtcgc   240
ccccttcacc ttggatcatg ttcaagaaat tgatgaaaa agaaaatgtg tccaactgca    300
tccagttgaa aacttcagtt attaagggta ttaagaatca attgatagag caatttccag   360
gtattgaacc atggcttaat caaatcatgc ctaagaaaga tcctgtcaaa atagtccgat   420
gccatgaaca tatagaaatc cttacagtaa atggagaatt actcttttt agacaaagag    480 aagggccttt ttatccaacc ctaagattac ttcacaaata tccttttatc ctgccacacc   540
agcaggttga taaaggagcc atcaaatttg tactcagtgg agcaaatatc atgtgtccag   600
gcttaacttc tcctggagct aagctttacc ctgctgcagt agataccatt gttgctatca   660
tggcagaagg aaaacagcat gctctatgtg ttggagtcat gaagatgtct gcagaagaca   720
ttgagaaagt caacaaagga attggcattg aaaatatcca ttatttaaat gatgggctgt   780
ggcatatgaa gacatataaa tgagcctcag aaggaatgca cttgggctaa atatggatat   840
tgtgctgtat ctgtgtttgt gtctgtgtgt gacagcatga agataatgcc tgtggttatg   900
ctgaataaat tcaccagatg ctaaaaaaaa aaaaaaaaa aaa                      943

<210> SEQ ID NO 8
<211> LENGTH: 181
<212> TYPE: PRT
<213> ORGANISM: Homo sapiens
<220> FEATURE:
<223> OTHER INFORMATION: MCT-1 Protein
```

<400> SEQUENCE: 8

```
Met Phe Lys Lys Phe Asp Glu Lys Glu Asn Val Ser Asn Cys Ile Gln
  1               5                  10                  15

Leu Lys Thr Ser Val Ile Lys Gly Ile Lys Asn Gln Leu Ile Glu Gln
                 20                  25                  30

Phe Pro Gly Ile Glu Pro Trp Leu Asn Gln Ile Met Pro Lys Lys Asp
             35                  40                  45

Pro Val Lys Ile Val Arg Cys His Glu His Ile Glu Ile Leu Thr Val
         50                  55                  60

Asn Gly Glu Leu Leu Phe Phe Arg Gln Arg Glu Gly Pro Phe Tyr Pro
 65                  70                  75                  80

Thr Leu Arg Leu Leu His Lys Tyr Pro Phe Ile Leu Pro His Gln Gln
                 85                  90                  95

Val Asp Lys Gly Ala Ile Lys Phe Val Leu Ser Gly Ala Asn Ile Met
                100                 105                 110

Cys Pro Gly Leu Thr Ser Pro Gly Ala Lys Leu Tyr Pro Ala Ala Val
            115                 120                 125

Asp Thr Ile Val Ala Ile Met Ala Glu Gly Lys Gln His Ala Leu Cys
        130                 135                 140

Val Gly Val Met Lys Met Ser Ala Glu Asp Ile Glu Lys Val Asn Lys
145                 150                 155                 160

Gly Ile Gly Ile Glu Asn Ile His Tyr Leu Asn Asp Gly Leu Trp His
                165                 170                 175

Met Lys Thr Tyr Lys
            180
```

<210> SEQ ID NO 9
<211> LENGTH: 58
<212> TYPE: PRT
<213> ORGANISM: Homo sapiens
<220> FEATURE:
<223> OTHER INFORMATION: Portion of MCT-1 protein sequence for
     comparison with Cyclin H protein sequence

<400> SEQUENCE: 9

```
Lys Glu Asn Val Ser Asn Cys Ile Gln Leu Lys Thr Ser Val Ile Lys
  1               5                  10                  15

Gly Ile Lys Asn Gln Leu Ile Glu Gln Phe Pro Gly Ile Glu Pro Trp
                 20                  25                  30

Leu Asn Gln Ile Met Pro Lys Lys Asp Pro Val Lys Ile Val Arg Cys
             35                  40                  45

His Glu His Ile Glu Ile Leu Thr Val Asn
         50                  55
```

<210> SEQ ID NO 10
<211> LENGTH: 50
<212> TYPE: PRT
<213> ORGANISM: Homo sapiens
<220> FEATURE:
<223> OTHER INFORMATION: Portion of Cyclin H protein sequence for
     comparison with MCT-1 protein sequence

<400> SEQUENCE: 10

```
Lys Glu Asn Arg Thr Cys Leu Ser Gln Leu Leu Asp Ile Met Lys Ser
  1               5                  10                  15

Met Arg Asn Leu Val Lys Lys Tyr Glu Pro Pro Arg Ser Glu Glu Val
                 20                  25                  30
```

-continued

```
Ala Val Leu Lys Gln Lys Leu Glu Arg Cys His Ser Ala Glu Leu Ala
        35                  40                  45

Leu Asn
    50
```